United States Patent
Imam

(10) Patent No.: US 10,182,994 B2
(45) Date of Patent: Jan. 22, 2019

(54) NANOPARTICULATE COMPLEX OF NICOTINE AND CERIUM OXIDE AND USE THEREOF

(71) Applicant: THE UNITED STATES OF AMERICA, AS REPRESENTED BY THE SECRETARY, DEPARTMENT OF HEALTH AND HUMAN SERVICES, Washington, DC (US)

(72) Inventor: Syed Imam, Little Rock, AR (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/317,743

(22) PCT Filed: Jun. 10, 2015

(86) PCT No.: PCT/US2015/035099
§ 371 (c)(1),
(2) Date: Dec. 9, 2016

(87) PCT Pub. No.: WO2015/191707
PCT Pub. Date: Dec. 17, 2015

(65) Prior Publication Data
US 2017/0105941 A1 Apr. 20, 2017

Related U.S. Application Data

(60) Provisional application No. 62/010,033, filed on Jun. 10, 2014.

(51) Int. Cl.
| | |
|---|---|
| *A61K 9/50* | (2006.01) |
| *A61K 9/51* | (2006.01) |
| *A61K 31/465* | (2006.01) |
| *A61K 33/24* | (2006.01) |
| *A61K 47/59* | (2017.01) |
| *A61K 47/64* | (2017.01) |
| *A61K 47/69* | (2017.01) |

(52) U.S. Cl.
CPC .......... *A61K 9/5052* (2013.01); *A61K 9/5031* (2013.01); *A61K 9/5115* (2013.01); *A61K 9/5169* (2013.01); *A61K 31/465* (2013.01); *A61K 33/24* (2013.01); *A61K 47/593* (2017.08); *A61K 47/6415* (2017.08); *A61K 47/6921* (2017.08)

(58) Field of Classification Search
CPC .. A61K 9/5052; A61K 9/5031; A61K 31/465; A61K 33/24
See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,837,028 | A | 6/1989 | Allen |
| 5,019,369 | A | 5/1991 | Presant et al. |
| 6,238,689 | B1 | 5/2001 | Rhodes et al. |
| 8,333,993 | B1 | 12/2012 | Perez et al. |
| 2007/0264487 | A1 | 11/2007 | Georgiades |
| 2008/0260824 | A1 | 10/2008 | Nangia et al. |
| 2010/0203142 | A1 | 8/2010 | Zhang et al. |
| 2011/0288132 | A1* | 11/2011 | Lindberg ........... A61K 31/4439 514/343 |
| 2011/0303871 | A1 | 12/2011 | Burba et al. |
| 2013/0017259 | A1* | 1/2013 | Azhir ................... A61K 31/465 424/461 |
| 2013/0251756 | A1* | 9/2013 | Self ....................... A61K 33/24 424/400 |

OTHER PUBLICATIONS

28. Pogocki et al. ("Application of nicotine enantiomers, derivatives and analogues in therapy of neurodegenerative disorders," in European Journal of Pharmacology, 563 (2007) pp. 18-39.*
Asati et al., "Oxidase Activity of Polymer-Coated Cerium Oxide Nanoparticles," *Angew. Chem. Int. Ed. Engl.* 48(13): 2308-2312 (2009).
Cimini et al., "Antibody-conjugated PEGylated cerium oxide nanoparticles for specific targeting of Aβ aggregates modulate neuronal survival pathways," *Acta Biomaterialia*, (8): 2056-2067 (2012).
European Patent Office, International Search Report issued in PCT/US2015/035099, dated Dec. 16, 2015, 4 pages.
European Patent Office, International Preliminary Report on Patentability, issued in PCT/US2015/035099, dated Dec. 22, 2016, 7 pages.
Giri et al., "Nanoceria: A Rar-Earth nanoparticle as a Novel Anti-Angiogenic Therapeutic Agent in Ovarian Cancer," *PLoS One*, 8(1):e54578 (2013).

(Continued)

*Primary Examiner* — Blessing M Fubara
(74) *Attorney, Agent, or Firm* — Klarquist Sparkman, LLP

(57) ABSTRACT

Disclosed are particles comprising a complex of nicotine and cerium oxide and a biodegradable coating comprising agglutinin. Also disclosed is a method of treating or preventing neurodegenerative or neurological disorders in a mammal in need thereof, comprising administering to the mammal a therapeutically effective amount of the particles.

13 Claims, No Drawings

(56) References Cited

OTHER PUBLICATIONS

Patil et al., "Synthesis of Nanocrystalline Ceria Particles for High Temperature Oxidation Resistant Coating," *Journal of Nanoparticle Research*, 4(5): 433-438 (2002).
Pogocki et al., "Application of nicotine enantiomers, derivatives and analogues in therapy of neurodegenerative disorders," *European Journal of Pharmacology*, 563: 18-39 (2007).
Quik et al, "Nicotine as a potential neuroprotective agent for Parkinson's disease," *Mov. Disord.* 27(8):947-957 (2012).
Szoka, Jr., et al., "Comparative properties and methods of preparation of lipid vesicles (liposomes)," *Ann. Rev. Biophys. Bioeng.* (9): 467-508 (1980).
Wong et al., "Catalytic Nanoceria are Preferentially Retained in the Rat Retina and are not Cytotoxic after Intravitreal Injection," *PLoS One*, 8 (3): e58431 (2013).

\* cited by examiner

NANOPARTICULATE COMPLEX OF NICOTINE AND CERIUM OXIDE AND USE THEREOF

CROSS-REFERENCE TO RELATED APPLICATIONS

This application is a U.S. National Phase of International Patent Application No. PCT/US2015/035099, filed Jun. 10, 2015, which claims the benefit of U.S. Provisional Patent Application No. 62/010,033, filed Jun. 10, 2014, the disclosures of which are incorporated by reference for all purposes.

BACKGROUND OF THE INVENTION

Neurodegeneration results from various different causes including genetic mutation, mitochondrial dysfunction, and the inability to handle increasing levels of oxidative or nitrosative stress can also lead to the progression of neurodegeneration. Substantial evidence from many in vitro and in vivo studies suggests that there is a commonality of events for the progression of many neurodegenerative diseases of aging. Some of these neurodegenerative diseases include Parkinson's disease (PD), Huntington's disease, Amyotrophic Lateral Sclerosis (ALS), and among the most common of the neurodegenerative disorders is Alzheimer's disease (AD). Mounting evidence in AD as well as in most neurodegenerative diseases shows an association with oxidative and nitrosative stress. Nitrosative stress and cell damage result when reactive nitrogen species (RNS) act together with reactive oxygen species (ROS).

Reactive oxygen species and reactive nitrogen species are formed during normal metabolism but an imbalance may result from the increased production of free radicals or from the failure of antioxidants and antioxidant enzymes to adequately scavenge the damaging molecules. This imbalance has been documented to be involved in AD. Several studies provide clear evidence that RNS, in particular peroxynitrite formation, contributes to the pathologies of chronic neurodegenerative diseases such as Parkinson's disease, AD, multiple sclerosis, and ALS. Peroxynitrite is formed from the reaction of nitric oxide radical with superoxide. Mitochondrial injury is believed to be a primary cause of peroxynitrite-promoting neurotoxic effects. Widespread peroxynitrite-mediated damage is seen in brain tissue from AD in the form of increased protein nitration in neurons.

However, the administration of antioxidants and antioxidant enzymes to treat diseases due to increased ROS and RNS in human clinical trials heretofore have been less than satisfactory due to issues with bioavailability and stability after administration.

The scientific community has known since 1959 that tobacco use has apparent protective effects against Parkinson's disease, and some animal models suggest that this protective effect arises from nicotine itself. Nicotine, therefore, represents a candidate "lead" neuroprotective drug for those diagnosed with early-stage PD. However, tremendous biological, political and ideological hurdles still apply to both smoking and the use of nicotine patches for treatment of PD. One of the main reasons for the unsuccessful clinical effect of nicotine in PD stems from the low degree of its bioavailability. While smoking, where nicotine is readily available to blood and then to brain, has been a powerful protective factor in the onset and progression of PD, nicotine patches do not replicate the protective effect due to its slow approach to the brain.

Thus, there remains an unmet need for improved methods for the prevention and/or treatment of neurodegeneration, in particular, Parkinson's disease.

BRIEF SUMMARY OF THE INVENTION

The invention provides particles comprising a complex of nicotine and cerium oxide and a biodegradable coating comprising agglutinin. The invention combines the advantages of nicotine and ceria nanoparticles to provide a therapeutic intervention to neurodegenerative or neurological disorders such as Parkinson's disease, Alzheimer's disease, amyotrophic lateral sclerosis, Friedreich's ataxia, Huntington's disease, dementia with Lewy bodies, multiple system atrophy, or neuroaxonal dystrophies. Ceria nanoparticles have a unique ability to switch oxidation states between III and IV. This ability to switch between oxidation states is comparable to that of biological antioxidants, thereby inparting to the ceria nanoparticles the very important biological property of radical scavenging. The biodegradable coating provides a sustained release of the particles and/or nicotine to neurons, in addition to imparting colloidal stability to the particles.

The invention also provides a method of treating or preventing neurodegenerative or neurological disorders in a mammal in need thereof, comprising administering to the mammal a therapeutically effective amount of particles comprising a complex of nicotine and cerium oxide and a biodegradable coating comprising agglutinin.

DETAILED DESCRIPTION OF THE INVENTION

The invention provides particles comprising a complex of nicotine and cerium oxide and a biodegradable coating comprising agglutinin.

The agglutinin can be any suitable agglutinin. An agglutinin is a substance that causes particles to coagulate to form a thickened mass. In certain embodiments, the agglutinin is a lectin. In certain preferred embodiments, the agglutinin is an N-acetylglucosamine binding lectin. In a certain preferred embodiment, the agglutinin is a wheat germ agglutinin.

In an embodiment, the agglutinin is conjugated to a polymer. In an embodiment, the polymer is a biodegradable polymer. The term "biodegradable" is used herein to refer to materials selected to dissipate upon implantation within a body or exposure to the environment, independent of which mechanisms by which dissipation can occur, such as dissolution, degradation, absorption and excretion. The terms "bioabsorbable," "resorbable" or "biodegradable" are used synonymously herein, unless otherwise specified, to refer to the ability of the material or its degradation products to be removed by biological events, such as by fluid transport away from the site of implantation or by cellular activity (e.g., phagocytosis or microbial degradation). In certain embodiments, the polymer is selected from polymers based on polylactide (PLA), polyglycolide (PGA), poly(lactic-co-glycolic acid (PLGA), polycaprolactone (PCL), their copolymers and mixtures thereof. Non-limiting examples of additional suitable polymers include chitosan, methyl cellulose, carboxy-methyl cellulose, poly vinyl acetate, alginate, polyethylene glycol (PEG), poly(2-hydroxyethyl methacrylate) (PHEMA), polymethyl methacrylate (PMMA), ethylene-vinyl acetate (EVA), polyacrylamide, and polyamine. In a certain preferred embodiment, the polymer is PGLA.

Advantageously, the agglutinin or the polymer-conjugated agglutinin provides a sustained release of the particles encapsulated therein, thereby allowing tailoring of the release profile to allow for delivery of the particles, when ingested orally, to selected sections of the alimentary tract. Additionally, the agglutinin or the polymer-conjugated agglutinin provides colloidal stability to the particles to allow for formulation in liquid suspension for oral or parenteral administration.

In certain embodiments, the agglutinin is labeled with a marker to provide for in vivo tracking. Any suitable marker can be used. For example, the marker can be a dye, such as a rhodamine dye. Examples of suitable rhodamine dyes include rhodamine B, rhodamine 6G, rhodamine 123, carboxytetramethyl rhodamine, tetramethyl rhodamine and its isothiocyanate derivative, sulforhodamine 101 and its acid chloride derivative, and rhodamine red. In a preferred embodiment, the marker is an isothiocyanate derivative of tetramethylrhodamine (TRITC).

In accordance with an embodiment, the ceria particles are nanoparticles, for example, the ceria particles have an average particle size in the range of 1 nm to 100 nm. In accordance with preferred embodiments, the ceria particles can have an average particle size of less than 20 nm, and more preferably in the range from about 1 nm to about 10 nm, e.g., from about 3 nm to about 5 nm.

The ceria nanoparticles can be synthesized by wet chemical process as previously described (S. Patil et al., 2002, *Journal of Nanoparticle Research* 4 (5): 433-438). For example, for the preparation of $CeO_2$ nanoparticles with increased ratio of $3^+/4^+$, $Ce(NO_3)_3.6H_2O$ is dissolved in $H_2O$ and $H_2O_2$ is rapidly added with stirring at 300 rpm. The solution is then heated at 150° C. with continuous stirring to obtain a light yellow colored stable dispersion of cerium oxide nanoparticles. The $CeO_2$ nanoparticles can be sonicated for 45-60 min prior to use to prevent agglomeration.

High resolution transmission electron microscopy can be used to analyze the size and morphology of the nanoparticles. Crystallinity of the nanoparticles can be assayed by using selected area electron diffraction pattern. Hydrodynamic size and surface charge can be analyzed by using dynamic light scattering. Surface chemistry and purity can be analyzed by X-ray photoelectron spectroscopy.

In accordance with another embodiment, the cerium oxide provided in the composition and method described herein comprise a reduced oxidation state of ceria molecules on surfaces of the nanoparticles. In reference to +3 versus +4 valence states, certain embodiments of the cerium oxide particles used include a greater number of +3 versus +4 valence states. In one embodiment, the cerium oxide comprises from about 10% to about 99% more $Ce^{3+}$ atoms versus $Ce^{4+}$ atoms. In another embodiment, the surface of the biocompatible material comprises at least about 10% more $Ce^{3+}$ atoms versus $Ce^{4+}$ atoms.

Nicotine can be electrostatically adsorbed on the surface of the nanoparticles. In some embodiments, the surface charge of the nanoparticles can first be modified by acid treatment. The nanoparticles can be washed with a solvent, for example, with water, and then incubated with nicotine. The nicotine-coated nanoparticles can be precipitated by adjusting the solution pH to about 8. The nicotine-coated nanoparticles can then be encapsulated inside poly(lactic-co-glycolic acid) (PLGA) particles. The amount of nicotine adsorbed on the surface can be quantified by using UV-VIS signature and thenno-gravimetric methods.

To encapsulate the nicotine-nanoparticle complex into poly(lactic-co-glycolic acid) (PLGA) particles, high molecular weight PLGA can be used for encapsulating the nicotine-nanoparticle complex using, for example, a double micro emulsion method (water-in-oil-in-water) in combination with solvent extraction and evaporation. The nicotine-nanoparticle complex can be dispersed in water and then emulsified in PLGA-dichloromethane. The resulting emulsion can then dispersed into a suitable water phase, for example, a polyvinyl alcohol water phase, with stirring to form a solution. Next, solvent extraction using, for example, dichloromethane can be carried out with stirring. PLGA microparticles encapsulated with the nicotine-nanoparticle complex can then be isolated by filtration and dried. The encapsulation efficacy can then be calculated to quantify the nicotine-nanoparticle complex loading into PLGA particles.

The conjugation of wheat germ agglutinin onto nicotine-nanoparticle encapsulated PLGA particles can be accomplished using any suitable method. In an embodiment, the carboxyl groups on the surface of nicotine-nanoparticle encapsulated PLGA particles can be coupled to the amine functional group present on the agglutinin using any coupling chemistry, for example, with 1-ethyl-3-[3-dimethyl-aminopropyl]carbodiimide hydrochloride (EDC) and N-hydroxysulfosuccinimide. The PLGA particles can be suspended in a suitable medium, for example, 2-(N-morpholino)ethanesulfonic acid (MES), NaCl, and pH 6 buffer. Coupling agents, for example, EDC and N-hydroxysulfosuccinimide can be added to the PLGA particles and the resulting mixture stirred at room temperature. Agglutinin (for example, wheat germ agglutinin) in a suitable buffer, for example, sodium phosphate buffer, can be then added to the reaction mixture and the resulting mixture stirred. In an embodiment, a 4:1 molar ratio of agglutinin:PLGA particles can be used for the reaction. PLGA particles conjugated with agglutinin can be recovered by centrifugation and subsequently washed. UV-Visible spectroscopy and Fourier transform infrared (FTIR) spectra can be collected to confirm the agglutinin conjugation.

To test how effective, safe and capable of preventing disease progression the nicotine-containing nanoparticles (NIC-NANO) can be, a well established animal model of PD can be used. It is contemplated that NIC-NANO-treatment can significantly slow the rate of disease progression and improve motor functions and dopaminergic phenotype in animal models of PD. Endpoints can evaluate the degree of various parameters that are currently used to define the progression of PD in human patients. It is expected that in this delivery form, nicotine (NIC) can modulate both autophagy and possibly mitophagy via nAChRα7 receptors and NANO will enhance anti-oxidant defense due to its superoxide dismutase (SOD)-mimetic properties. The biodegradable coating provides slow and sustained release of nicotine to neurons.

The compound can be administered to a patient in the form of a pharmaceutical composition comprising a pharmaceutically acceptable carrier and the nicotine-cerium oxide-agglutinin complex described herein.

It is preferred that the pharmaceutically acceptable carrier be one that is chemically inert to the nicotine-cerium oxide-agglutinin complex and one that has no detrimental side effects or toxicity under the conditions of use.

The choice of carrier will be determined in part by the particular compound of the present invention chosen, as well as by the particular method used to administer the nicotine-cerium oxide-agglutinin complex. Accordingly, there is a wide variety of suitable formulations of the pharmaceutical composition of the present invention.

Formulations suitable for oral administration can consist of (a) liquid solutions, such as a therapeutically effective amount of the inventive compound dissolved in diluents, such as water, saline, or orange juice, (b) capsules, sachets, tablets, lozenges, and troches, each containing a predetermined amount of the nicotine-cerium oxide-agglutinin complex, as solids or granules, (c) powders, (d) suspensions in an appropriate liquid, and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

In some embodiments, the formulation can be suitable to prolonging the amount of time that the nicotine-cerium oxide-agglutinin complex of the present invention is in contact with the alimentary tract of the mammal. In this regard, various formulations such as extended release formulation and formulations designed to prolong the amount of time that the nicotine-cerium oxide-agglutinin complex is retained in the stomach before release into the small intestine can be utilized. A number of suitable formulations is presented in *Remington: The Science and Practice of Pharmacy*.

In some embodiments, the nicotine-cerium oxide-agglutinin complex of the present invention can be administered in the form of a food additive, that is, in admixture with foodstuffs or beverages. For use as a food additive, the compound or salt can be mixed with a foodstuff or beverage per se, or can be formulated as a composition comprising one or more suitable excipients prior to mixing with a foodstuff or beverage. The foodstuff or beverage can be any suitable foodstuff or beverage. In some embodiments, the foodstuff or beverage has a relatively high fat content.

It will be appreciated by one of ordinary skill in the art that, in addition to the aforedescribed pharmaceutical compositions, the nicotine-cerium oxide-agglutinin complex of the present invention may be formulated as inclusion complexes, such as cyclodextrin inclusion complexes, or liposomes. Liposomes serve to target the nicotine-cerium oxide-agglutinin complex to a particular tissue, such dendritic cells. Liposomes can also be used to increase the half-life of the inventive nicotine-cerium oxide-agglutinin complex. Liposomes useful in the present invention include emulsions, foams, micelles, insoluble monolayers, liquid crystals, phospholipid dispersions, lamellar layers and the like. In these preparations, the active agent to be delivered is incorporated as part of a liposome, alone or in conjunction with a suitable chemotherapeutic agent. Thus, liposomes filled with a desired inventive nicotine-cerium oxide-agglutinin complex, can be directed to the site of a specific tissue type, dendritic cells, for example, where the liposomes then deliver the selected compositions. Liposomes for use in the invention are formed from standard vesicle-forming lipids, which generally include neutral and negatively charged phospholipids and a sterol, such as cholesterol. The selection of lipids is generally guided by consideration of for example, liposome size and stability of the liposomes in the blood stream. A variety of methods are available for preparing liposomes, as described in, for example, Szoka et al., *Ann. Rev. Biophys. Bioeng.*, 9, 467 (1980), and U.S. Pat. Nos. 4,235,871, 4,501,728, 4,837,028, and 5,019,369. For targeting to the cells of a particular tissue type, a ligand to be incorporated into the liposome can include, for example, antibodies or fragments thereof specific for cell surface determinants of the targeted tissue type. A liposome suspension containing a nicotine-cerium oxide-agglutinin complex of the present invention may be administered intravenously, locally, topically, etc. in a dose that varies according to the mode of administration, the agent being delivered, and the stage of disease being treated.

In certain embodiments, the pharmaceutical composition can be administered parenterally, e.g., intravenously, subcutaneously, intradermally, or intramuscularly. Thus, the invention provides compositions for parenteral administration that comprise a solution or suspension of the inventive nicotine-cerium oxide-agglutinin complex dissolved or suspended in an acceptable carrier suitable for parenteral administration, including aqueous and non-aqueous isotonic sterile injection solutions. Many such compositions are known in the art.

Preferably, the animal is a mammal. More preferably, the mammal is a human.

The term "mammal" includes, but is not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human.

The invention further provides a method of treating or preventing neurodegenerative or neurological disorders in a mammal in need thereof, comprising administering to the mammal a therapeutically effective amount of the inventive particles. The neurodegenerative or neurological disorder can be any neurodegenerative or neurological disorder that is responsive to the treatment with the inventive particles. In certain embodiments, the neurodegenerative or neurological disorder is mediated, at least in part, via acetylcholine receptors. In certain embodiments, the neurodegenerative or neurological disorder is one where problems of protein aggregation or degradation, generation of oxidative stress resulting from reactive oxygen or nitrogen species, autophagy and neuroinflammation lead to neuronal injury. In certain embodiments, the neurodegenerative or neurological disorder can be characterized by the abnormal accumulation of aggregates of alpha-synuclein protein in neurons, nerve fibers or glial cells, which are referred to as synucleinopathies. In certain embodiments, the neurodegenerative or neurological disorder is Parkinson's disease, Alzheimer's disease, amyotrophic lateral sclerosis, Friedreich's ataxia, Huntington's disease, dementia with Lewy bodies, multiple system atrophy, or neuroaxonal dystrophies. In a preferred embodiment, the neurodegenerative or neurological disorder is Parkinson's disease.

The dose administered to a mammal, particularly, a human, in accordance with the present invention should be sufficient to effect the desired response. Such responses include reversal or prevention of the undesirable effects of the disease or disorder for which treatment is desired or to elicit the desired benefit. In certain embodiments, the disorder is a neurodegenerative disease, for example, Parkinson's disease. One skilled in the art will recognize that dosage will depend upon a variety of factors, including the age, condition, and body weight of the human, as well as the extent of the Parkinson's disease in the human. The size of the dose will also be determined by the route, timing and frequency of administration as well as the existence, nature, and extent of any adverse side-effects that might accompany the administration of the nicotine-cerium oxide-agglutinin complex and the desired physiological effect. It will be appreciated by one of skill in the art that successful treatment of the Parkinson's disease or other disease or disorder may require prolonged treatment involving multiple administrations.

Suitable doses and dosage regimens can be determined by conventional range-finding techniques known to those of ordinary skill in the art. Generally, treatment is initiated with smaller dosages that are less than the optimum dose of the nicotine-cerium oxide-agglutinin complex. Thereafter, the dosage is increased by small increments until the optimum effect under the circumstances is reached. The present inventive method typically will involve the administration of about 0.1 to about 300 mg (e.g., about 0.1 to about 150 mg, about 0.1 to about 100 mg, or about 0.1 to about 50 mg) of the nicotine-cerium oxide-agglutinin complex described above per kg body weight of the mammal.

The therapeutically effective amount of the nicotine-cerium oxide-agglutinin complex administered can vary depending upon the desired effects and the factors noted above. Typically, dosages will be between 0.01 mg/kg and 250 mg/kg of the subject's body weight, and more typically between about 0.05 mg/kg and 100 mg/kg, such as from about 0.2 to about 80 mg/kg, from about 5 to about 40 mg/kg or from about 10 to about 30 mg/kg of the subject's body weight. Thus, unit dosage forms can be formulated based upon the suitable ranges recited above and the subject's body weight. The term "unit dosage form" as used herein refers to a physically discrete unit of therapeutic agent appropriate for the subject to be treated.

Alternatively, dosages are calculated based on body surface area and from about 1 $mg/m^2$ to about 200 $mg/m^2$, such as from about 5 $mg/m^2$ to about 100 $mg/m^2$ will be administered to the subject per day. In particular embodiments, administration of the therapeutically effective amount of the nicotine-cerium oxide-agglutinin complex involves administering to the subject from about 5 $mg/m^2$ to about 50 $mg/m^2$, such as from about 10 $mg/m^2$ to about 40 $mg/m^2$ per day. It is currently believed that a single dosage of the nicotine-cerium oxide-agglutinin complex is suitable, however a therapeutically effective dosage can be supplied over an extended period of time or in multiple doses per day. Thus, unit dosage forms also can be calculated using a subject's body surface area based on the suitable ranges recited above and the desired dosing schedule.

Example 1

This example demonstrates a method of preparation of preparation of cerium oxide nanoparticles with enhanced surface area in accordance with an embodiment of the invention.

Surface enhanced ceria nanoparticles are prepared by a wet chemical method. Briefly, 99.999% cerium oxide nanoparticles are dissolved in double distilled water ($ddH_2O$) and then a stoichiometric amount of hydrogen peroxide is added to the solution to form cerium oxide nanoparticles. The process is carried out in a biological safety cabinet, using autoclaved water and glassware to maintain sterility. The above synthesized ceria is then thoroughly characterized. High resolution transmission electron microscopy is used to analyze the size and morphology of the nanoparticles. Crystallinity of the nanoparticles is assayed by selected area electron diffraction pattern. Hydrodynamic size and surface charge are analyzed by using dynamic light scattering. Surface chemistry and purity are analyzed by X-ray photoelectron spectroscopy.

Example 2

This example demonstrates a method of nicotine-nanoceria (NIC-NANO) complex formation in accordance with an embodiment of the invention.

Nicotine is electrostatically adsorbed on the surface of the ceria nanoparticles. Surface charge of the nanoparticles is modified by acid treatment. In particular, 1N nitric acid is used to adjust the pH of the solution to 3. The thus-treated nanoparticles are thoroughly washed by double distilled water ($ddH_2O$) and incubated with nicotine. Nicotine-coated nanoceria particles are subjected to pH adjustment by changing the solution pH to about 8. The nicotine-nanoceria can then be encapsulated inside poly(lactic-co-glycolic acid) (PLGA) particles. The amount of nicotine adsorbed on the surface is quantified by UV-VIS signature and theretogravimetric methods.

Example 3

This example demonstrates a method of encapsulation of nicotine-NANO complex (nicotine-nanoceria complex) into poly(lactic-co-glycolic acid) (PLGA) in accordance with an embodiment of the invention.

High molecular weight PLGA (lactide:gycolide 50:50; 40,000-75,000 molecular weight) is used for encapsulating the nicotine-NANO complex using double micro emulsion method (water-in-oil-in-water) in combination with solvent extraction and evaporation. The nicotine-NANO complex is dispersed in water and then emulsified in PLGA-dichloromethane (DCM). This emulsion is then dispersed into polyvinyl alcohol (PVA) water phase under vigorous stirring. A dichloromethane extraction is carried out for 5 hr with stirring by transferring the solution to a large volume of cold water. PLGA encapsulated nicotine-NANO complex micro particles are filtered and dried under vacuum. Encapsulation efficacy is then calculated to quantify the nicotine-NANO complex loading into PLGA particles.

Example 4

This example demonstrates a method of conjugation of wheat agglutinin on nicotine-NANO encapsulated PLGA particles in accordance with an embodiment of the invention.

The carboxyl groups on the surface of nicotine-NANO encapsulated PLGA particles are coupled to the amine functional groups present in the agglutinin using the 1-Ethyl-3-[3-dimethylaminopropyl]carbodiimide hydrochloride (EDC) and N-hydroxysulfosuccinimide (Sulfo NHS) coupling chemistry. PLGA particles are suspended in 0.05M MES, 0.05M NaCl, pH 6 buffer. 2 mM EDC and 5 mM Sulfo-NHS are added to the PLGA particles and stirred at room temperature. Agglutinin in sodium phosphate buffer is added to the reaction mixture and stirred. 4:1 molar ratio of agglutinin:PLGA particles are used for the reaction. PLGA particles conjugated with agglutinin are recovered by centrifugation and after through washing. UV-Visible spectroscopy and Fourier transform infrared (FTIR) spectroscopy are utilized to confirm the agglutinin conjugation.

Example 5

This example demonstrates a method of prevention of neurotoxic damage to neurons induced by the neurotoxin MPP+.

Lentiviral shRNA technology has been used to 'knock down' or render silent the major components of cellular autophagy in neurons. It has been observed that such 'knocked down' neurons are more prone to the type of cellular damage seen in Parkinson's disease.

A lentiviral shRNA was used to knock-down the expression of ATG7, a component of the autophagy system. Pretreatment of these neurons that have low expression of ATG7 with nicotine, by itself, was observed to prevent MPP+ induced cellular damage. Pretreatment of these neurons with nicotine in the presence of nanoceria provided an enhanced prevention of MPP+ cellular damage as compared with pretreatment with nicotine by itself. The prevention afforded by nicotine and nanoceria against MPP+ induced cellular damage was reflected by increased cell survival.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. Particles comprising a complex of nicotine and cerium oxide and a biodegradable coating comprising agglutinin conjugated to a polymer.

2. The particles of claim 1, wherein the cerium oxide comprises cerium oxide nanoparticles.

3. The particles of claim 2, wherein the cerium oxide nanoparticles have an average particle size from about 1 to about 10 nm.

4. The particles of claim 1, wherein the cerium oxide comprises at least about 10% more $Ce^{3+}$ atoms versus $Ce^{4+}$ atoms.

5. The particles of claim 1, wherein the agglutinin is a wheat germ agglutinin.

6. The particles of claim 1, wherein the polymer is poly(lactic-co-glycolic) acid.

7. The particles of claim 1, wherein the polymer comprises a label.

8. The particles of claim 7, wherein the label comprises a dye.

9. The particles of claim 8, wherein the dye is selected from rhodamine B, rhodamine 6G, rhodamine 123, carboxytetramethyl rhodamine, tetramethyl rhodamine, tetramethyl rhodamine isothiocyanate, sulforhodamine 101, sulforhodamine 101 acid chloride, and rhodamine red.

10. A pharmaceutical composition comprising the particles of claim 1 and a pharmaceutically acceptable carrier.

11. A method of treating a neurodegenerative or neurological disorder in a mammal in need thereof, comprising administering to the mammal a therapeutically effective amount of the particles of claim 1.

12. The method of claim 11, wherein the neurodegenerative or neurological disorder is Parkinson's disease, Alzheimer's disease, amyotrophic lateral sclerosis, Friedreich's ataxia, Huntington's disease, dementia with Lewy bodies, multiple system atrophy, or neuroaxonal dystrophies.

13. The method of claim 11, wherein the neurodegenerative or neurological disorder is Parkinson's disease.

* * * * *